(12) United States Patent
Ross, Jr. et al.

(10) Patent No.: US 6,770,624 B2
(45) Date of Patent: Aug. 3, 2004

(54) TREATMENT OF HEART FAILURE WITH GROWTH HORMONE

(75) Inventors: John Ross, Jr., La Jolla, CA (US); Kenneth R. Chien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 256 days.

(21) Appl. No.: 09/938,853

(22) Filed: Aug. 23, 2001

(65) Prior Publication Data

US 2002/0068700 A1 Jun. 6, 2002

Related U.S. Application Data

(63) Continuation of application No. 08/869,237, filed on Jun. 4, 1997, now Pat. No. 6,306,826.

(51) Int. Cl.[7] .......................... A61K 38/27; C07K 14/61
(52) U.S. Cl. .............................. 514/12; 514/2; 530/399
(58) Field of Search ........................ 514/2, 12; 530/399

(56) References Cited

U.S. PATENT DOCUMENTS

| | | | |
|---|---|---|---|
| 4,670,393 A | | 6/1987 | Seeburg |
| 5,019,400 A | | 5/1991 | Gombotz et al. |
| 5,595,882 A | | 1/1997 | Fujisawa et al. |
| 5,610,134 A | | 3/1997 | Clark et al. |
| 6,306,826 B1 | * | 10/2001 | Ross et al. .................... 514/12 |

FOREIGN PATENT DOCUMENTS

| | | |
|---|---|---|
| WO | WO 90/04788 | 5/1990 |
| WO | WO 92/09690 | 6/1992 |
| WO | WO 94/12158 | 6/1994 |
| WO | WO 95/28173 | 10/1995 |
| WO | WO 96/40072 | 12/1996 |
| WO | WO 96/40256 | 12/1996 |
| WO | WO 96/40257 | 12/1996 |
| WO | WO 96/40258 | 12/1996 |

OTHER PUBLICATIONS

Duerr, R., et al., 1995, "Insulin–like Growth Factor–1 Enhances Ventricular Hypertrophy and Function during the Onset of Experimental Cardiac Failure," *J. Clin. Invest.* 95:619–27.

Duerr, R., et al., 1996, "Cardiovascular Effects of Insulin–like Growth Factor–1 and Growth Hormone in Chronic Left Ventricular Failure in the Rat," *Circulation* 93: 2188–96.

Fazio, S. et al., 1996, "A Preliminary Study of Growth Hormone in the Treatment of Dilated Cardiomyopathy," *New Engl. J. Med.* 334:809–14.

Jin, H. et al., 1995, "Beneficial Effects of Growth Hormone and Insulin–like Growth Factor–1 in Experimental Heart Failure in Rats Treated with Chronic ACE Inhibition," *J. Cardiovasc. Pharmacol.* 26: 420–5.

Schieffer, B. et al., 1994, "Comparative Effects of Chronic Angiotensin–Converting Enzyme Inhibition and Angiotensin Type 1 Receptor Blockade on Cardic Remodeling After Myocardial Infarction in the Rat," *Circulation* 89: 2273–82.

Wong, P.C. et al., 1992, "Angiotensin II Receptor Antagonists and Receptor Subtypes," *Trends Endocrinol. Metab.* 3:211–7.

Yang, R. et al., 1995, "Growth Hormone Improves Cardiac Performance in Experimental Heart Failure," *Circulation* 92: 262–7.

Duerr, R., et al., "Cardiovascular Effects of Insulin–Like Growth Factor–1 and Growth Hormone in Chronic Left Ventricular Failure in the Rat", *Circulation*, (Jun. 15, 1996), vol. 93(12):2188–2196.

Hongo, M. et al., "Angiotensin II Blockade Followed by Growth Hormone as Adjunctive Therapy After Experimental Myocardial Infarction", *Journal of Cardiac Failure*, (Sep. 1998), vol. 4(3):213–224.

Osterziel, M. et al., "Randomised, Double–blind, Placebo–controlled Trial of Human Recombinant Growth Hormone in Patients with Chronic Heart Failure due to Dilated Cardiomyopathy", *The Lancet*, (Apr. 25, 1998), vol. 351:1233–1237.

Ross, John et al., "The Role of Hypertrophy and Growth Factors in Heart Failure", *Journal of Cardiac Failure*, (Dec. 1996), vol. 2(4S):S121–S128.

* cited by examiner

*Primary Examiner*—Christine J. Saoud
(74) *Attorney, Agent, or Firm*—Karl Bozicevic; Bozicevic, Field & Francis LLP

(57) ABSTRACT

Heart failure following myocardial infarction is treated by administration of an angiotensin II inhibitor for 8–12 weeks, followed by administration of a growth hormone for 1-3 weeks.

21 Claims, No Drawings

TREATMENT OF HEART FAILURE WITH GROWTH HORMONE

CROSS REFERENCE

This application is a continuation application of Ser. No. 08/869,237, filed Jun. 4, 1997 (issued as U.S. Pat. No. 6,306,826 on Oct. 23, 2001). which is incorporated herein by reference in its entirety and to which application we claim priority under 35 USC §120.

BACKGROUND OF THE INVENTION

Heart failure occurs in three to four million individuals annually in the United States, and is a highly important cause of cardiac morbidity and mortality. In about 60% of the patients, the heart failure is secondary to late stage coronary disease, and in most of the remainder it is due to primary myocardial disease in the form of idiopathic dilated cardiomyopathy. Treatment for severe heart failure has improved with the addition of angiotensin converting enzyme (ACE) inhibitors to standard therapy, but despite such treatment the outlook remains poor in symptomatic patients (mortality about 10% per year), and limiting cardiac symptoms often persist. Cardiac transplantation is a definitive therapy for severe heart failure in some individuals, but there is a need for new adjunctive medical therapies to improve functional status and provide a more favorable prognosis. Previous findings in animal models, and a recent study in patients with heart failure, showing favorable effects of growth hormone (GH) suggest that GH treatment may offer such an adjunctive measure. Bunting et al., WO95/28173 disclosed treatment of congestive heart failure by administration of GH. Clark et al., U.S. Pat. No. 5,610,134 disclosed treatment of congestive heart failure by administration of GH and insulin-like growth factor 1 ("IGF1"), with or without an angiotensin II converting enzyme (ACE) inhibitor. However, our studies in animals with heart failure have shown that an ACE inhibitor in high dose may diminish the beneficial effects of GH, including its action to promote a physiologic form of hypertrophy.

SUMMARY OF THE INVENTION

We have now invented a new method for treating heart failure which follows myocardial infarction by administering an angiotensin II ($AT_1$) receptor blocker for 8–12 weeks, followed thereafter by administration of a growth hormone for 1–3 weeks.

DESCRIPTION OF THE PREFERRED EMBODIMENTS

The term "cardiac ischaemia" as used herein refers to the interruption of oxygen supply to the cardiac muscle (which may be acute or chronic). Cardiac ischaemia caused by obstruction can lead to myocardial infarction. A large myocardial infarction, in turn, can lead to heart failure, a condition in which the function of the left ventricle is impaired and inadequate to meet the body's needs at rest or during stress. Heart failure can be due to other functions as well, or of unknown etiology (idiopathic).

The term "angiotensin II inhibitor" refers to a compound capable of inhibiting or reducing the activity or effect of angiotensin II (the active form of angiotensin). Angiotensin II inhibitors include compounds which bind, inhibit, or compete for $AT_1$ receptors (described by Fujisawa et al., U.S. Pat. No. 5,595,882, incorporated herein by reference). An exemplary, presently preferred $AT_1$ inhibitor is losartan. Other $AT_1$ inhibitors may be identified by determining their binding affinity to the $AT_1$ receptor as set forth in U.S. Pat. No. 5,595,882.

The term "ventricular remodeling" refers to the alteration in chamber size, wall thickness, and other dimensional changes which occur in response to myocardial damage.

The term "growth hormone" in general refers to a protein or polypeptide, whether natural, recombinant, or chemical in origin, which is capable of stimulating the growth or proliferation of normal cells under appropriate conditions. "GH" and "hGH" refer to human growth hormone and its variations, including Protropin® (Genentech Inc.), Nutropin® (Genentech, Inc.), placental GH (U.S. Pat. No. 4,670,393), and the variants described in WO90/04788 and WO92/09690, all incorporated herein by reference. GH may also be modified, for example by conjugation with polyoxyethylene ("PEG") to form "PEGylated GH" as described in '134. Another growth factor which is endogenous and mediates some of the effects of growth hormone is insulin-like growth factor-1 (IGF- 1). IGF-1 has been administered as an alternative for growth hormone in treating rats with heart failure, as described by R. Duerr et al., *J Clin Invest* (1995) 95:619–27. IGF-1 may be used in conjunction with or in lieu of GH in the practice of the invention.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The term "subject" as used herein refers to a mammal, particularly a mammal having heart failure, preferably a human.

We have now developed a method for maximizing the effect of GH treatment for heart failure following myocardial infarction. Angiotensin II effects were inhibited for 2½ months after myocardial infarction using a specific blocker of the angiotensin type 1 ($AT_1$) receptor which is known to inhibit post-infarction hypertrophy and unfavorable remodeling of the left ventricle (LV), reduce myocardial fibrosis, and improve the cardiac output in this experimental model of heart failure. Such effects occurred in the present study and effects of remodeling after 2½ months of $AT_1$ treatment alone were detected at 2 weeks after the $AT_1$ blocker was discontinued compared to untreated animals. In another group of rats, following $AT_1$ receptor blockade with losartan for 2½ months after myocardial infarction, GH was then given alone for 2 weeks. In this setting, GH significantly improved myocardial contractility and LV performance, increased LV muscle mass and wall thickness, enhanced LV diastolic function, and increased the cardiac output and cardiac index (collectively "favorable remodeling"). "Favorable remodeling" is an improvement in any of the above-mentioned functions or parameters of at least 20% over post-infarction levels, preferably at least 25% or greater. Thus, following acute myocardial infarction an initial sustained inhibition of the unfavorable effects of angiotensin II on remodeling is followed by GH, in a sequential manner, and constitutes a new treatment for heart failure. This sequential treatment may be repeated cyclicly if desired.

Suitable angiotensin II inhibitors will reduce or eliminate unfavorable remodeling effects. Presently preferred angiotensin II inhibitors are $AT_1$ receptor blockers, for example losartan. Suitable growth hormones will improve cardiac function, improving one or more of myocardial contractility, LV performance, LV muscle mass, LV wall thickness, LV diastolic function, cardiac output and cardiac index. The presently preferred growth hormone is human growth hormone (hGH). Suitable therapeutics may also be examined using an animal model, for example as described in the Examples below. Animal models are well-developed, and fairly predictive of success in humans.

Following diagnosis of ischemic damage, an angiotensin II inhibitor is prescribed at a dosage determined in view of the patient's condition, weight, severity of symptoms, and the like. Angiotensin II inhibitors include ACE inhibitors, such as captopril or enalapril, and $AT_1$ receptor blockers such as losartan (others, such as valrantan and irbesartan are in clinical efficacy trials), prescribed at a dosage determined by the patient's condition. The typical starting dose ranges from about 2.5 mg/day to about 20 mg/day for ACE inhibitors such as enalapril, and about 12.5 mg/day to about 50 mg/day for $AT_1$ inhibitors such as losartan. Treatment with the angiotensin II inhibitor is continued until substantial beneficial remodeling of the heart occurs, or until the period for unfavorable remodeling has passed. Treatment is preferably continued until remodeling is complete (about 10 to about 12 weeks), or may be continued indefinitely, particularly if heart failure is present. The patient's recovery progress may be monitored using standard techniques, for example echocardiography. At this point, administration of the angiotensin II inhibitor can be discontinued (as it may also inhibit the effect of the growth hormone), or relatively low dose ACE inhibition or $AT_1$ blockade maintained. The selected growth hormone is thus administered until the desired effect is achieved, typically from about two to about three weeks, preferably about two weeks. However, growth hormone was safely administered for three months to patients with idiopathic dilated cardiomyopathy on unknown doses of ACE inhibitors. The presently preferred growth hormone is hGH (Protropin®, Genentech), administered at a dosage of about 2 to about 6 IU, preferably about 4 IU every other day. Another suitable GH is Nutropin® (Genentech Inc.), administered at a dosage of about 1 to about 3 $\mu$g, preferably about 2 $\mu$g every other day. Again, the patient's recovery progress may be monitored using standard techniques. If desired, the process may be repeated.

Suitable compositions or devices comprising growth hormone include those suitable for controlling blood levels of growth hormone. For example, compositions or devices for the prolonged or controlled delivery of GH over the period of time disclosed herein are useful in the context of the present invention. A preferred means for controlling blood levels of GH is to administer the GH in the form of a polymeric matrix that releases GH as a consequence of diffusion from and/or degradation of a polymer implant.

A variety of biodegradable and non-biodegradable polymers have been used for such applications, including polyesters such as poly(lactide-co-glycolide)s, polyorthoesters and ethylenevinyl acetate polymers. In general the delivery of the GH is controlled by the selection of the appropriate polymer, polymerization conditions, drug loading and the presence or absence of various excipients.

Particularly preferred among the compositions for prolonged delivery of GH include bioerodible polymers such as poly(lactide), poly(lactide-co-glycolide), poly(caprolactone), polycarbonates, polyamides, polyanhydrides, polyamino acids, polyorthoesters, polyacetals, polycyanoacrylates and degradable polyurethanes and non-erodible polymers such as polyacrylates, ethylene-vinyl acetate polymers and other acyl substituted cellulose acetates and derivatives thereof, non-erodible polyurethanes, polystyrenes, polyvinylchloride, polyvinylfluoride, poly(vinyl imidazole), chlorosuphonated polyolefins, and polyethylene oxide.

Preferred biodegradable polymers are aliphatic polyesters, e.g., homopolymers or copolymers synthesized from one or more kinds of -hydroxycarboxylic acids (e.g., glycolic acid, lactic acid, 2-hydroxybutyric acid, etc.), hydroxydicarboxylic acids (e.g., malic acid, etc.) and hydroxytricarboxylic acids (e.g., citric acid, etc.), or their mixtures, and the like. When the -hydroxycarboxylic acids are chiral compounds, they may be any of D-, L- and DL-configuration. It is preferable that the ratio of the D-/L-configuration (mol %) is in the range of about 75/25 to about 25/75. More preferred is a hydroxycarboxylic acid wherein the ratio of the D-/L- configuration (mol %) is in the range of about 60/40 to about 30/70.

Examples of -hydroxycarboxylic acid polymers are lactic acid-glycolic acid copolymer and 2-hydroxybutyric acid-glycolic acid copolymer. A particularly preferred—hydroxycarboxylic acid copolymer is a lactic acid-glycolic acid.

The polylactic acid preferably has a weight average molecular weight of about 1,000 to about 100,000. More preferred is a polymer acid having the weight average molecular weight of about 5,000 to about 70,000. Particularly preferred is a polylactic acid having the weight average molecular weight of about 6,000 to about 15,000.

The compositional ratio (lactic acid/glycolic acid, mol %) in the lactic acid-glycolic acid copolymer is preferably about 100/0 to about 40/60, more preferably about 90/10 to about 45/55, and most preferably about 60/40 to about 40/60. The weight average molecular weight of the lactic acid-glycolic acid copolymer is preferably about 3,000 to about 20,000, and more preferably about 4,000 to about 15,000.

Preferred compositions are described in, for example WO94/12158, which disclosure is specifically incorporated herein by reference.

Growth hormone is particularly suited for complexing with various metal cations having a valency of $2^+$ or more. These compositions are suitable for the methods described herein. The metal cations include polyvalent metals such as zinc (II), iron (II, III), copper (II), tin (II, IV), and aluminum (II, III) with an inorganic or organic acid. The metal is preferably a polyvalent metal, and more preferably an alkaline earth metal: particularly preferred metals are calcium and zinc.

Polyvalent metal salts that may be used include salts of zinc with an inorganic acid, e.g., zinc halides (for example, zinc chloride, bromide, iodide, or fluoride), zinc sulfate, zinc nitrate, zinc thiocyanate, etc.; salts of zinc with an organic acid, e.g., aliphatic carboxylic acid zinc salts (e.g., zinc carbonate, acetate, glycolate, lactate, tartrate, etc.), aromatic zinc salts (e.g., zinc benzoate, salicylate, phenolsulfonate, etc.); salts of calcium with an inorganic acid, e.g., calcium halide (e.g., calcium chloride, bromide, iodide, fluoride, etc.), calcium sulfate, nitrate, thiocyanate, etc.; salts of calcium with an organic acid, e.g., aliphatic carboxylic acid calcium salt (e.g., calcium carbonate, acetate, propionate, oxalate, tartrate, lactate, citrate, gluconate, etc.) and aromatic calcium salts (e.g., calcium benzoate, salicylate, etc.).

The preferred polyvalent metal salt includes zinc acetate and zinc carbonate. When the GH contains a metal, the molar ratio of metal cation to GH is between about 4:1' and about 10:1 and more preferably about 6:1. Preferred compositions of GH comprising zinc are described in WO96/40072.

The biodegradable polymer composition can be produced by emulsifying and dispersing an aqueous solution or solid form of GH or a metal salt in an organic solvent solution of a biodegradable or non-biodegradable polymer to prepare a water/oil (w/o) or oil/water (o/w) emulsion or an organic solution or suspension of a biodegradable polymer containing a metal salt. The resulting substances are washed and dried or subjected to an in-water drying method, phase separation method, spray drying method or the like with washing and drying. Methods for producing a biodegradable or non-biodegradable polymer are well known in the art and include: In-water drying method (water/oil/water or w/o/w method), in-water drying method (o/w method), phase separation method (Coacervation method), and the spray drying method. Preferred among the methods of preparation are those described in U.S. Pat. No. 5,019,400 to Gombotz et al., specifically incorporated herein by reference.

The concentration of GH comprised in the sustained-release preparation in the present invention is, for example, about 0.1 to about 30% (w/w), and preferably about 10% to about 20% (w/w).

The sustained-release preparation may be administered in the form of microcapsules or in various dosage forms such as non-oral preparations (e.g., intramuscular-, subcutaneous- or visceral- injectable or nasal-, rectal or uterine-transmucosal preparation), or oral preparations (e.g., capsules such as hard capsule and soft capsule, solid preparations such as in granules and powder, liquid preparations such as suspensions).

The particularly preferred sustained-release preparation is administered by injection. To prepare an injection using the microcapsules obtained above, the microcapsules may be formulated with a dispersant (e.g., surfactants such as Tween® 80, HCO-60; polysaccharides such as carboxymethylcellulose, sodium alginate, sodium hyaluronate; protamine sulfate; polyethylene glycol 400, etc.), a preservative (e.g., methyl paraben, propyl paraben, etc.), an isotonizing agent (e.g., sodium chloride, mannitol, sorbitol, glucose, etc.), and a local anesthetic (e.g., xylocaine hydrochloride, chlorobutanol, etc.) to provide an aqueous suspension, or dispersed with vegetable oil (e.g., sesame oil, corn oil, etc.), or a mixture thereof with a phospholipid (e.g., lecithin) or medium-chain fatty acid triglycerides (e.g., Migriol 812) to provide an oily suspension.

When the sustained-release preparation comprises microcapsules, the microcapsules are preferably fine particles. The size of microcapsules for an injectable suspension may be selected from the range satisfying the requirements for the degree of dispersion and passage through the needle used for the injection. For example, the microcapsule particle size may be within the range of about 0.1 to about 300 $\mu$m, preferably about 1 to about 150 $\mu$m and more preferably about 2 to about 100 $\mu$m.

Methods of preparing microcapsules as a sterile preparation include, but are not limited to, the method in which the entire production process is sterile, the method in which gamma rays are used as the sterilant, and method in which an antiseptic is added during the manufacturing process.

The sustained-release preparation can be safely used in mammals (e.g., humans, bovine, swine, dogs, cats, mice, rats, rabbits, etc.).

When the sustained-release preparation is a one-week-long action formulation, the dosage of the bioactive polypeptide can be chosen from the range of about 0.0001 to about 10 mg/kg body weight per an adult. The more preferred dosage can be suitably chosen from the range of about 0.0005 to about 1 mg/kg body weight. The preferred administration frequency of the sustained-release preparation depend on the dosage form, the duration of the release, the subject animal species and other factors.

EXAMPLES

The following examples are set forth so as to provide those of ordinary skill in the art with a complete disclosure and description of how to practice the invention, and are not intended to limit the scope of the invention. Efforts have been made to ensure accuracy with respect to numbers used (e.g., amounts, temperature, molecular weight, etc.), but some experimental errors and deviation should be accounted for. Unless indicated otherwise, parts are parts by weight, molecular weight is weight average molecular weight, temperature is in degrees Centigrade, and pressure is at or near atmospheric.

Example 1

Normal Rats: Normal female Sprague Dawley rats (240–260 g each) were randomized to one of the following four groups: rats receiving placebo for 6 weeks (Control group, n=8); rats treated with placebo for 6 weeks with concomitant rhGH (2 mg/kg bid) for the final 2 weeks (GH group, n=8); rats treated with relatively low-dose losartan (L) (20 mg/kg/day in drinking water) for 6 weeks with concomitant rhGH (2 mg/kg/bid, SC) during the final 2 weeks (LowL+GH, n=8); and rats treated with high dose L (2 g/L in drinking water) for 6 weeks with concomitant rhGH (2 mg/kg/bid, SC) during the final 2 weeks (HighL+GH, n=8). In these 32 animals, the responses of body weight (BW) and the weights of the heart and other selected organs were then examined.

MI Rats: Female Sprague-Dawley rats (230–260 g each) were anesthetized with a mixture of ketamine hydrochloride (100 mg/kg) and xylazine (10 mg/kg) given intraperitoneally. Complete occlusion of the proximal left coronary artery was performed as described by R. Duerr et al., *J Clin Invest* (1995) 95:619–27; and R. L. Duerr et al., *Circulation* (1996) 93:2188–96. Briefly, animals were placed in the supine position, intubated and respired with a rodent ventilator. A left thoracotomy was performed, the pericardium opened and the left coronary artery, which is intramural, was encircled within the myocardium between the left atrial appendage and the right ventricular outflow tract with a curved needle and 5-0 silk suture. Upon tying the ligature, complete occlusion was evidenced by a distinct regional color change of the myocardium, together with the development of acute ST segment elevations on the electrocardiogram (ECG). The chest was then closed in layers and the pneumothorax evacuated.

Following the operation, animals were caged in proportion to size, given water and standard rat chow ad libitum, and housed in a climate-controlled environment subjected to 12 hour light/dark cycles. Of the 120 animals subjected to surgery, 76 (63%) survived to the seventh postoperative day and showed clear ECG and echocardiographic evidence of myocardial infarction. They were then randomly assigned to one of the following three groups: rats receiving no treatment for 12 weeks (Control group, n=29); rats treated with losartan (L, 2 g/L in drinking water) for 10 weeks followed by rhGH alone (2 mg/kg, bid SC) for 2 weeks (GH[L] group, n=21); and rats treated with L for 10 weeks with placebo (given bid) for the final two weeks (P[L] group, n=26). The last group was included primarily to assess the degree of left ventricular remodeling and function that might persist for 2 weeks after losartan was discontinued, at the time that the control and GH(L) groups were compared.

Echocardiographic examinations were performed just before randomization at one week, and again at 13 weeks after coronary ligation, prior to terminal hemodynamic studies. Animals were anesthetized in the same manner as described for surgery. The chest was shaved and rats were examined in the left lateral recumbent position. The instrument used was an annular array system (Apogee CX, ATL Interspec, Bothell, Wash.) with the transducer operating at 7.5 MHZ, at a minimum depth setting of 3 cm and sector width of 40–50 degrees to optimize resolution and penetration for 2-D and M-mode imaging (see N. Tanaka et al., *Circulation* (1996) 94:1109–17). Parasternal short-axis views of the left ventricle (LV) at the level of the papillary muscles were obtained, and two-dimensional guided M-mode echocardiographic tracings were recorded at paper speeds of 50 to 100 mm/s. Left ventricular anterior and posterior wall thickness (AWT, PWT) at end-diastole (ED) and LV internal dimensions (D) at end-systole and ED were measured according to criteria recommended by the American Society of Echocardiography (D. J. Sahn et al., *Circulation* (1978) 58:1072–83) and LV percent (%) fractional shortening (FS) was calculated.

For pulsed wave Doppler examination, the minimum sample volume (0.6 mm) was used and the pulse repetition frequency was 5 KHZ. We measured the ratio of peak A velocity to peak E velocity (A/E) of transmittal flow and the deceleration time (DT) of the E wave, which was defined as the time from the E wave peak to a linear extrapolation of the velocity signal to baseline, using a modified parasternal long-axis view (S. E. Litwin et al., *Circulation* (1994) 89:345–54). Also, in 30 normal, age-matched female Sprague-Dawley rats M-mode and pulsed wave Doppler echocardiographic studies were performed.

Infarct size was estimated by histologic analysis of multiple LV sections and echocardiography in animals, the latter by observing the akinetic portion of the LV in the short axis view and calculating the ratio of the akinetic portion of the LV endocardial circumference to that of the entire circumference on stop-frame 2D images at ED.

Tracings were recorded on videotape, a digital color printer (Sony, EP-1800MD), or a black and white thermal printer (Sony, UP-870MD), all measurements being made in a blinded manner.

Within 3 days after the second echocardiographic study, the rats were anesthetized, intubated, and mechanically ventilated in the supine position as described above. Under closed-chest conditions, a 2 Fr high-fidelity catheter-tip micromanometer (model SPR-407, Millar, Houston, Tex.) was passed into the LV via the right carotid artery to measure the LV pressure; its first derivative was also monitored using an electronic differentiating circuit. Zero baseline reference for the catheter was obtained by placing the sensor in a 32□C water bath for at least 30 min before insertion and after withdrawal. Because of the occasional drift in the LV ED pressure signal with the high-fidelity catheter, in some rats a fluid-filled catheter (PE 50) also was inserted in the LV to measure LV ED pressure. A similar fluid-filled catheter was inserted into the left carotid artery to record the aortic pressure in all rats. Pressure data were transcribed on a chart recorder and digitized data were recorded simultaneously at a sampling rate of 2000/sec using Cordis software (Dataq Instruments, Inc., Akron, Ohio). Hemodynamic variables (LV peak and ED pressure and LV $dP/dt_{max}$) were analyzed by averaging at least 10 consecutive beats with the aid of Cordat software (Dusseldorf, Germany). The time constant of LV isovolumic pressure decay (Tau) was calculated according to a variable asymptote method (G. L. Raffet al., *Circ Res* (1981) 48:813–24). The equation simplifies to $P=P_0 \exp(-t/T)+P_B$, $dP/dt=-1/T(P-P_B)$, where $P_0$ is pressure and $P_B$ is the intercept of pressure at time zero and T is tau. T is determined from the inverse slope of the linear relation dP/dt versus $(P-P_B)$.

Cardiac output was measured in subgroups of animals using 15 μm fluorescent labeled microspheres, as described by R. L. Duerr (1996) supra. In brief, under anesthetized conditions as described above, the right carotid artery was cannulated and a PE 50 tubing advanced into the LV. An incision was made over the right groin, and a PE 50 tubing advanced via the femoral artery into the right common iliac artery. The microspheres were suspended in 10 ml of 0.1% Tween® 80 and 0.9% saline (Molecular Probes, Inc., Eugene, Oreg.), and vials were vortexed at room temperature for a minimum of 20 min prior to injection to insure adequate mixing. Reference blood sampling via the femoral artery catheter was commenced 15 to 20 seconds prior to injection and continued for a minimum of 30 sec after flushing the LV catheter. Approximately $2.9 \times 10^4$ spheres in 0.3 ml were injected into the LV over a 15 second period using a Hamilton injection syringe, and the syringe and LV catheter were flushed with 1 ml of normal saline for an additional 20 to 30 sec. The reference sample volume was equivalent to the volume of the microsphere suspension and saline injected (1.3 ml). Using this method, measurements of cardiac output were performed in triplicate in each animal. Fluorescent dye present in each sample was measured on a Perkin Elmer LS50B luminescence spectrometer. The photomultiplier tube voltage was set at 820 V and the excitation and emission slit widths were set at 4 and 5 nm, respectively. A cutoff filter eliminated all light below 350 um wavelength, as described by R. L. Duerr (1996) supra.

After the hemodynamic measurements, the rats were euthanized and wet weights of heart and other selected organs, including liver, spleen, and kidney, were measured. Cardiac fixation was then performed as described by R. L. Duerr (1996) supra. In brief, polyethylene catheters were introduced into the LV apex and the descending aorta. The LV chamber was filled from a reservoir and maintained at 10 mmHg. After washout of blood from the coronary arteries with heparinized saline, the myocardium was perfused retrogradely from the aorta with 10% buffered formalin at a constant pressure of 60 mmHg for 20 minutes. The heart was then excised and immersed in 10% formalin for 24 hours. Subsequently, the atria and adhesions were dissected away and the right ventricle (RV) and LV were separated and weighted, the interventricular septum being included with the LV. The right tibia was dissected and its length from the condyles to the tip of the medial malleolus was measured with a micrometer caliper by the method of Yin et al., *Am J Physiol* (1982); 243. To compare heart weights among groups, the weights were normalized by tibial length (TL) as well as by body weight (BW).

The LV was sectioned from the apex to base in a parallel line to the atrioventricular groove into four slices 2 to 2.5 mm in thickness, which were embedded in paraffin. Sections 10 μm thick were cut, mounted and stained with Masson's trichrome. These four slides were then analyzed blindly to assess infarct size, the slides being projected with a microprojector (Jena, Germany) at a magnification of ×13 and measurements made using computerized planimetry. The percent infarct size was determined from the ratio of the sum of the scar lengths along the endocardial and epicardial surfaces to the sum of the total endocardial and epicardial circumferences (T. E. Raya et al., *Am J Hypertens* (1991) 4:334S–40S).

In order to confirm $AT_1$ receptor blockade with losartan, angiotensin II dose-response curves for changes in carotid arterial pressure were carried out in an additional 14 female Sprague-Dawley rats (260–300 g/each). Eight rats were normal, 4 untreated and 4 treated for 2 weeks with losartan (2 g/L in drinking water). In 6 rats a large MI was produced 3 to 4 weeks prior to study, of which 3 received losartan (2 g/L in drinking water) for 2 weeks and 3 were untreated. Losartan treatment for 2 weeks produced marked rightward shifts of the angiotensin II-blood pressure dose-response curves in both untreated normal rats and in rats with chronic MI.

The last dose of GH was given 4 to 6 hours before the hemodynamic study. Just prior to euthanasia, 1 ml of blood was obtained in a heparinized syringe from the LV cavity and centrifuged, the plasma obtained and stored at $-70°C$ for subsequent analysis. Human GH was measured by a sensitive and specific ELISA assay (A. C. Celniker et al., *J Clin Endocrinol Metab* (1989) 68:469–76), which does not detect rat GH. Total IGF-1 levels were measured after acid-ethanol extraction by radioimmunoassay, using human IGF-1 (Genentech M3-RD1) as the standard and a rabbit anti-IGF-1 polyclonal antiserum (R. W. Furlanetto et al., *J Clin Invest* (1977) 60:648–57) as described by R. Yang et al., *Circulation* (1995) 92:262–67; H. Jin et al., *J Cardiovasc Pharmacol* (1995) 26:420–25.

Among the 76 rats randomized to the experimental protocol, 10 animals (6 Controls, one from the P(L) group, 3 in the GH(L) group) died during the treatment, and 5 (one Control, one P(L), and 3 GH(L) group) did not have clear histologic evidence of myocardial infarction or showed a very small infarct size (<20%) despite prior ECG and echocardiographic evidence of infarction early after coronary occlusion, yielding 61 animals for analysis (22 in the Control group, 19 in the P(L) group, and 20 in the GH(L) group).

In 17 of the 61 animals, the quality of one or more of the 4 histologic sections was found to be unsatisfactory for measuring infarct size. In 36 of the rats having both 2D echocardiographic and histologic assessments of infarct size, we obtained a good correlation between the methods (y=0.46x+21.5, r=0.77, p<0.001), also interobserver variability of infarct size by the 2D method showed good agreement by two observers, with a mean difference of 0.86% and coefficient of variation of 10.26%. Therefore, we used histologic measurements of myocardial infarct size in 44 animals, and in the 17 animals in which histological assessment was not feasible infarct size was estimated by 2D echocardiography.

Data are shown below expressed as mean ±SD, except for the dose-response effects of angiotensin II on blood pressure (mean ±SEM). Intergroup comparisons between controls, GH(L), and P(L) groups in the rats with MI were made using an analysis of variance with post hoc tests by the Neuman-Keuls multiple range method. Two-tailed unpaired t-tests were used to compare variables in untreated control MI rats with those in normal rats (different numbers of rats having each measurement), and the groups of normal rats were compared using two-tailed t-tests with Bonferonni corrections. All data were analyzed in a blinded fashion. A probability value of P<0.05 was accepted as statistically significant.

Results:

The BW and weights of selected organs were significantly increased in the GH, LowL+GH and HighL+GH groups compared with those in the control group, without significant differences among the 3 groups receiving GH (Table 1).

TABLE 1

Body, organ and cardiac weights in normal rats after $AT_1$ blockade and GH

| | Control | GH | Low L + GH | High L + GH |
|---|---|---|---|---|
| Number | 8 | 8 | 8 | 8 |
| BW (g) | 273.7 ± 17.6 | 319.9 ± 15.9* | 310.8 ± 17.5* | 328.4 ± 26.7* |
| Liver (g) | 10.20 ± 1.25 | 13.69 ± 0.94* | 13.77 ± 1.17* | 14.18 ± 1.94* |
| Spleen (g) | 0.77 ± 0.10 | 1.21 ± 0.10* | 1.10 ± 0.19* | 1.09 ± 0.17* |
| Kidney (g) | 1.99 ± 0.13 | 2.30 ± 0.19* | 2.42 ± 0.19* | 2.34 ± 0.11* |
| TL (cm) | 3.96 ± 0.06 | 4.05 ± 0.08 | 3.96 ± 0.07 | 3.99 ± 0.06 |
| HW (g) | 1.31 ± 0.10 | 1.42 ± 0.12* | 1.40 ± 0.13 | 1.22 ± 0.06** |
| HW/BW (%) | 0.48 ± 0.03 | 0.45 ± 0.04 | 0.45 ± 0.03 | 0.37 ± 0.04*,** |
| HW/TL (%) | 33.0 ± 2.6 | 35.1 ± 2.5* | 35.3 ± 3.3 | 30.6 ± 1.9** |
| LV wt (g) | 0.96 ± 0.10 | 1.04 ± 0.06 | 1.02 ± 0.07 | 0.92 ± 0.08** |
| LV/BW (%) | 0.35 ± 0.03 | 0.33 ± 0.01 | 0.33 ± 0.02 | 0.28 ± 0.04* |
| LV/TL (%) | 24.2 ± 2.5 | 25.7 ± 1.6 | 25.8 ± 1.8 | 23.2 ± 2.1** |
| RV wt (g) | 0.23 ± 0.05 | 0.26 ± 0.02 | 0.25 ± 0.04 | 0.24 ± 0.05 |
| RV/BW (%) | 0.08 ± 0.02 | 0.08 ± 0.01 | 0.08 ± 0.01 | 0.07 ± 0.01 |
| RV/TL (%) | 5.8 ± 1.4 | 6.3 ± 0.6 | 6.2 ± 1.0 | 6.0 ± 1.2 |

BW = body weight; LV = left ventricle; RV = right ventricle; HW = heart weight; TL = tibia length.
Heart weight was measured before fixation; RV and LV weights were measured after fixation.
Values are mean ± SD.
*p < 0.05 vs. Control, and **p < 0.05 vs GH group by paired t test with Bonferroni correction.

At 13 weeks, adequate echocardiographic tracings were obtained in 21 control rats, 19 in the P(L) group and 20 in the GH(L) group. Hemodynamic variables were successfully measured in 20 Control rats, 17 in the GH(L) group, and 19 in the P(L) group, while cardiac output was measured in subgroups of 8 control rats, 10 rats in the GH(L) group, and 6 in the P(L) group. Serum levels of rhGH and IGF-1 were measured in 16 control rats, 16 in the GH(L) group and 15 rats in the P(L) group.

In the HighL+GH group, the heart weight, absolute and normalized to the BW and TL, were significantly decreased compared to the GH group, and the LV weights, absolute and normalized to TL also were significantly decreased (Table 1). The heart weights and LV weights, absolute and normalized to the BW and to the TL, were not significantly different between the GH and LowL+GH groups. The RV weights, absolute and normalized to the BW and to the TL were not significantly different among all 4 groups. In the GH group, absolute heart weights, and heart weight normalized to TL (but not to BW) were significantly increased compared to those in the control group.

These data provide evidence that in the normal rat, the hypertrophic cardiac effect of GH is blocked by high dose but not by relatively low dose losartan.

Myocardial infarct size in all 61 rats averaged 42.6±7.7% of the LV circumference at 13 weeks after coronary artery ligation, and there were no significant differences in the average infarct size among controls and the two treatment groups (Table 2).

In the GH(L) group, the average serum rhGH level obtained early after GH injection was markedly increased, and the average IGF-1 level was significantly elevated (by 34%) compared to control rats with infarction.

Treatment for 2 weeks with GH following L (the GH(L) group) caused significant increases in the body weight (BW) (13% compared to controls), and in the weights of selected organs including the liver, spleen, and kidney, compared with those in controls and to the group treated with placebo for 2 weeks after L (the P(L) group). The BW and organ weights did not differ significantly between the control and P(L) groups.

Heart and ventricular weights, absolute and normalized to the BW and to the TL, are summarized in Table 2. The LV weight/BW ratio was significantly reduced compared to controls in both the GH(L) and the P(L) groups, whereas the reductions in heart weight/BW were not significant; the LV weight normalized to the TL was reduced in the P(L) group compared to controls.

TABLE 2

Myocardial Infarct size, Hormone Levels, and Body, Organ, Cardiac weights in rats with Myocardial Infarction

|  | Control | P(L) | GH(L) |
|---|---|---|---|
| Number | 22 | 19 | 20 |
| infarct size (%) | 41.6 ± 7.6 | 42.3 ± 7.5 | 41.1 ± 8.0 |
| GH (ng/ml) | 0.9 ± 0.2 | 0.9 ± 0.2 | 16684 ± 1250*+ |
|  | (n = 16) | (n = 15) | (n = 16) |
| IGF-1 (ng/ml) | 298.6 ± 80.5 | 338.5 ± 64.3 | 399.2 ± 127.1* |
|  | (n = 16) | (n = 15) | (n = 16) |
| BW (g) | 278.6 ± 18.1 | 277.7 ± 18.8 | 314.8 ± 33.3*+ |
| Liver (g) | 9.36 ± 1.44 | 8.91 ± 1.12 | 12.72 ± 1.44*+ |
| Spleen (g) | 0.93 ± 0.18 | 0.95 ± 0.16 | 1.38 ± 0.33*+ |
| Kidney (g) | 1.94 ± 0.23 | 1.99 ± 0.20 | 2.23 ± 0.19*+ |
| TL (cm) | 4.02 ± 0.10 | 4.03 ± 0.09 | 4.03 ± 0.10 |
| HW (g) | 1.70 ± 0.41 | 1.47 ± 0.25 | 1.62 ± 0.37 |
| HW/BW (%) | 0.61 ± 0.16 | 0.53 ± 0.09 | 0.51 ± 0.12 |
| HW/TL (%) | 42.4 ± 10.2 | 36.4 ± 6.3 | 40.3 ± 9.1 |
| LV wt (g) | 0.98 ± 0.17 | 0.87 ± 0.10 | 0.95 ± 0.17 |
| LV wt/BW (%) | 0.35 ± 0.06 | 0.32 ± 0.04* | 0.30 ± 0.06* |
| LV wt/TL (%) | 24.5 ± 4.1 | 21.7 ± 2.5* | 23.5 ± 4.4 |
| RV wt (g) | 0.26 ± 0.12 | 0.21 ± 0.04 | 0.29 ± 0.12+ |
| RV wt/BW (%) | 0.10 ± 0.05 | 0.08 ± 0.01 | 0.09 ± 0.04 |
| RV wt/TL(%) | 6.6 ± 3.1 | 5.2 ± 0.9 | 7.2 ± 3.0+ |

Control, rats with myocardial infarction untreated for 12 weeks; P(L) = treatment with placebo (P) for two weeks following 10 weeks of losartan (L); GH(L) = treatment with GH for 2 weeks following 10 weeks of L. GH = growth hormone, IGF-1 = insulin-like growth factor 1, BW = body weight, TL = tibia length, HW = heart weight, RV = right ventricle, LV = left ventricle, wt = weight. Heart weight was measured before fixation, LV and RV weights were measured after fixation.
*p < 0.05 for P(L) group and GH(L) group vs control group, +p < 0.01 for GH(L) group vs P(L) group. Values are mean ± SD.

The RV weight, absolute and normalized to the TL, was increased significantly in the GH(L) group compared to that in the P(L) group, and was not significantly different from controls.

Heart rate and LV systolic and mean aortic pressures were closely similar among the three groups (Table 3). LV end-diastolic pressure (EDP) was elevated in controls (11.9 vs 3.7 mmHg in 17 normal rats, P<0.01) (Table 4). The reduction in LVEDP was not significant in the GH(L) group compared with controls but it was significantly reduced in the P(L) group (Table 3). LV dP/dt$_{max}$ was reduced in controls (4699 vs 6545 mmHg/s in 17 normal rats, p<0.001) (Table 4). LV dP/dt$_{max}$ was significantly greater in the GH(L) group than in controls, but it was not significantly increased in the P(L) group (Table 3). Tau was shortened compared to controls in both the GH(L) and P(L) groups (Table 3).

TABLE 3

Hemodynamic Characteristics in Rats with Myocardial Infarction

|  | Control | P(L) | GH(L) |
|---|---|---|---|
| Pressures: |  |  |  |
| Number | 20 | 19 | 17 |
| HR (bpm) | 244.8 ± 36.7 | 242.3 ± 47.5 | 250.9 ± 24.1 |
| LVEDP (mmHg) | 11.9 ± 7.7 | 3.9 ± 2.1* | 8.5 ± 7.7 |
|  | (n = 16) | (n = 10) | (n = 11) |
| LVSP (mmHg) | 93.1 ± 15.6 | 93.8 ± 18.1 | 95.6 ± 16.1 |
| Mean AoP (mmHg) | 78.0 ± 11.5 | 75.0 ± 13.2 | 79.3 ± 13.7 |
| Lv dP/dt$_{max}$ (mmHg/s) | 4699 ± 1004 | 5045 ± 667 | 5579 ± 1063* |
| Tau (ms) | 34.8 ± 7.5 | 25.7 ± 8.1* | 22.1 ± 7.9* |
|  | (n = 15) | (n = 19) | (n = 16) |
| Cardiac Output: |  |  |  |
| Number | 8 | 6 | 10 |
| CO (ml/min) | 40.6 ± 7.3 | 47.9 ± 5.3 | 58.0 ± 11.9*+ |
| CI (ml/min/kg) | 148.5 ± 24.9 | 178.5 ± 18.9* | 189.0 ± 31.0* |
| SV (ml/beat) | 0.18 ± 0.03 | 0.20 ± 0.02 | 0.25 ± 0.04*+ |
| SVI (ml/beat/kg) | 0.65 ± 0.11 | 0.73 ± 0.07 | 0.81 ± 0.10* |
| Mean AoP (mmHg) | 76.8 ± 13.7 | 76.4 ± 12.0 | 66.7 ± 10.8 |
| SVR (mmHg/ml/min) | 1.92 ± 0.39 | 1.61 ± 0.31 | 1.17 ± 0.18* |

HR = heart rate, LVEDP = left ventricular end-diastolic pressure, LVSP = left ventricular systolic pressure, AoP = aortic pressure, LV dP/dt$_{max}$ = maximal first derivative of left ventricular pressure, Tau = time constant of LV pressure fall, CO = cardiac output, CI = cardiac index, SV = stroke volume, SVI = stroke volume index, SVR = systemic vascular resistance.
*p < 0.05 for P(L) group and GH(L) group vs control group, +p < 0.01 for GH(L) group vs P(L) group. Values are mean ± SD.

The cardiac index was reduced in controls (148.5 vs. 214.7 ml/min/kg in normal rats, p<0.05, Table 4). The cardiac output and the stroke volume were significantly increased in the GH(L) group compared to controls and the P(L) group. The CI was significantly higher in both the GH(L) and P(L) groups than in controls, but the systemic vascular resistance was significantly reduced (by 39%) only in the GH(L) group (Table 3).

TABLE 4

Hemodynamic and Echo findings in normal rats and rats with myocardial infarction

|  | Normal | MI (control) | p value |
|---|---|---|---|
| Pressures: |  |  |  |
| LVEDP (mmHg) | 3.7 ± 2.2 | 11.9 ± 7.7 | <0.01 |
|  | (n = 17) | (n = 16) |  |
| LVSP (mmHg) | 105.2 ± 21.0 | 93.1 ± 15.6 | p = 0.052 |
|  | (n = 17) | (n = 20) |  |
| Mean AoP (mmHg) | 89.3 ± 17.7 | 78.0 ± 11.5 | p < 0.05 |
|  | (n = 17) | (n = 20) |  |
| LV dP/dt$_{max}$ (mmHg/s) | 6545 ± 943 | 4699 ± 1004 | p < 0.001 |
|  | (n = 17) | (n = 20) |  |
| Tau (ms) | 13.6 ± 1.8 | 34.8 ± 7.5 | p < 0.001 |
|  | (n = 14) | (n = 15) |  |
| CI (ml/min/kg) | 214.7 ± 55.4 | 148.5 ± 24.9 | p < 0.05 |
|  | (n = 5) | (n = 8) |  |
| SVR (mmHg/ml/min) | 1.44 ± 0.46 | 1.92 ± 0.39 | p <0.05 |
|  | (n = 5) | (n = 8) |  |

TABLE 4-continued

Hemodynamic and Echo findings in normal rats and rats with myocardial infarction

|  | Normal | MI (control) | p value |
|---|---|---|---|
| Echocardio-graphic Data: | | | |
| EDD (mm) | 6.08 ± 0.54 (n = 30) | 9.97 ± 1.12 (n = 21) | p < 0.001 |
| FS (%) | 41.0 ± 6.3 (n = 30) | 15.4 ± 6.0 (n = 21) | p < 0.001 |
| DT (ms) | 57.6 ± 16.7 (n = 30) | 38.3 ± 7.6 (n = 21) | p < 0.001 |

MI = myocardial infarction, control group, untreated rats with MI. LVEDP = left ventricular end-diastolic pressure, LVSP = left ventricular systolic pressure, AoP = aortic pressure, LV = left ventricle, LV $dP/dt_{max}$ = maximal first derivative of left ventricular pressure, Tau = time constant of LV pressure fall, CI = cardiac index, SVR = systemic vascular resistance, EDD = end- diastolic dimension, FS = fractional shortening of left ventricle, DT = deceleration time of E wave of transmitral flow velocity. Numbers are mean ± SD.

The EDD of the LV was significantly increased in controls (9.97 vs 6.08 mm in normal rats, p<0.001), and the % FS was reduced (15.4% vs. 41.0% in normal rats, p<0.001, Table 4). The absolute EDDs were not significantly different in the 3 groups, but the EDD/BW was reduced in the GH(L) group versus the control and P(L) groups (Table 5). In the GH(L) group, the % FS of the LV was significantly greater than in controls. The anterior wall thickness (AWT) (the infarcted wall) was abnormally thin and similar among the groups, whereas the non-infarcted posterior wall thickness (PWT) was significantly greater in the GH(L) group than in the other two groups, resulting in a significant decrease in the EDD/PWT ratio compared with the control and P(L) groups (table 5).

The A/E ratio of Doppler-determined mitral flow velocity tended to be lower in the control group compared with the other groups, but the differences were not significant (table 4). The deceleration time (DT) of the E wave was shortened in controls (38.3 vs. 57.6 ms in 30 normal rats, p<0.001). The DT was significantly prolonged in both the GH(L) and P(L) groups compared to controls (Table 5).

TABLE 5

M-Mode and Doppler Echocardiographic Findings in Rats with Myocardial Infarction

|  | Control | P(L) | GH(L) |
|---|---|---|---|
| Number | 21 | 19 | 20 |
| EDD (mm) | 9.97 ± 1.12 | 9.52 ± 1.16 | 9.91 ± 0.42 |
| EDD/TL | 0.25 ± 0.03 | 0.24 ± 0.03 | 0.25 ± 0.01 |
| EDD/BW (mm/g) | 0.036 ± 0.005 | 0.035 ± 0.004 | 0.032 ± 0.004*+ |
| EDD/PWT | 7.97 ± 1.83 | 7.29 ± 1.28 | 6.76 ± 0.99* |
| ESD (mm) | 8.47 ± 1.36 | 7.86 ± 1.20 | 7.90 ± 0.72 |
| FS (%) | 15.4 ± 6.0 | 17.7 ± 5.3 | 20.3 ± 5.6* |
| AWT (mm) | 0.81 ± 0.15 | 0.80 ± 0.19 | 0.79 ± 0.15 |
| PWT (mm) | 1.28 ± 0.17 | 1.33 ± 0.16 | 1.49 ± 0.19*+ |
| A/E ratio | 0.40 ± 0.27 | 0.53 ± 0.15 | 0.45 ± 0.29 |
| DT (ms) | 38.3 ± 7.6 | 44.7 ± 5.6* | 48.5 ± 9.8* |

All variables refer to the left ventricle. EDD = end-diastolic dimension at LV chamber, TL = tibial length, BW = body weight, PWT = posterior wall thickness at end-diastole, AWT = anterior wall thickness at end-diastole, ESD = end-systolic dimension at LV chamber, FS = fractional shortening, A/E ratio = ratio of peak transmitral A velocity to peak E velocity, DT = deceleration time of E wave of transmitral flow velocity.
*p < 0.05 vs control group, +p < 0.05 GH(L) group vs P(L). Values are mean ± SD.

In this study, experimental LV failure at approximately 3 months after coronary ligation in untreated rats with myocardial infarctions that involved more than 20% of the LV circumference was characterized by a reduced cardiac index, markedly increased LV cavity dimension, increased LVEDP, severely reduced LV fractional shortening and LV $dP/dt_{max}$, and impairment of LV relaxation (tau) and early filling, when compared to normal rats.

The data demonstrates that after favorable LV remodeling had been induced by $AT_1$ receptor blockade for 10 weeks, GH administration alone for 2 weeks was associated with (1) improved stroke volume and cardiac index, (2) decreased system vascular resistance, (3) increased LV fractional shortening, (4) modest enhancement of LV myocardial contractility (LV $dP/dt_{max}$), (5) a hypertrophic effect on the LV which contributed to an improved ratio of LV diastolic dimension to wall thickness, and (6) improved LV relaxation (tau) and early diastolic filling rate. Further, some of these effects, particularly those on diastolic function and the cardiac index, undoubtedly received a contribution from a persistent favorable action of $AT_1$ blockade, evident in rats in which losartan was replaced by placebo for 2 weeks.

The instant invention is shown and described herein at what is considered to be the most practical and preferred embodiments. It is recognized, however, that departures may be made therefrom which are within the scope of the invention and that obvious modifications will occur to one skilled in the art upon reading this disclosure.

What is claimed:

1. A method for treating heart failure in a subject, comprising:

a) administering an angiotensin II ($AT_1$) receptor inhibitor to said subject for a first period beginning at about the time of a myocardial infarction;

b) reducing administration of said angiotensin II ($AT_1$) receptor inhibitor after said initial period; and c) administering human growth hormone during a second period beginning after said reducing administration of said $AT_1$ receptor inhibitor.

2. The method of claim 1, wherein said first period has a duration of about 10 to 12 weeks.

3. The method of claim 1, wherein the $AT_1$ receptor inhibitor is administered at least once daily.

4. The method of claim 1, wherein $AT_1$ receptor inhibitor administration is discontinued following said first period.

5. The method of claim 1, wherein said $AT_1$ receptor inhibitor comprises losartan.

6. The method of claim 1, wherein said growth hormone is administered for about two weeks to about three months.

7. The method of claim 1, wherein said reducing of $AT_1$ receptor inhibitor allows for a favorable physiologic hypertrophic effect from said growth hormone.

8. A method of treating heart failure in a subject, comprising;

a) administering an angiotensin II ($AT_1$) receptor inhibitor to said subject over a first period beginning about the time of an ischemic event, and said first period continuing for a sufficient amount of time to substantially permit favorable left ventricular remodeling or limit unfavorable ventricular remodeling;

b) decreasing said administering of $AT_1$ receptor inhibitor at a time approximately after said ventricular remodeling; and c) administering human growth hormone to said subject during a second period beginning at a time approximately after said ventricular remodeling.

9. The method of claim 8, wherein administering said $AT_1$ receptor inhibitor is discontinued at about the time administering said growth hormone begins.

10. The method of claim 8, wherein the angiotensin II ($AT_1$) receptor inhibitor is administered at least once daily.

11. The method of claim 8, wherein administration of said $AT_1$ receptor inhibitor is discontinued at about the time administering said growth hormone begins.

12. The method of claim 8, wherein said administration of said $AT_1$ receptor inhibitor following said ventricular remodeling is decreased prior to the end of said first period.

13. The method of claim 8, wherein said $AT_1$ receptor inhibitor comprises losartan.

14. The method of claim 8, wherein said growth hormone is human growth hormone.

15. The method of claim 8, wherein said $AT_1$ receptor inhibitor is administered beginning within seven days of said ischemic event.

16. The method of claim 8, wherein said $AT_1$ receptor inhibitor is administered for about 8 to about 12 weeks.

17. The method of claim 8, wherein said $AT_1$ receptor inhibitor is administered for about 10 weeks.

18. The method of claim 8, wherein said growth hormone is administered for about two weeks to about three months.

19. The method of claim 8, wherein a second administration of a composition comprising $AT_1$ receptor inhibitor is administered for a time following said growth hormone administration.

20. The method of claim 19, wherein growth hormone is administered following said second administration of $AT_1$ receptor inhibitor.

21. The method of claim 8, wherein decreasing said administering of $AT_1$ receptor inhibitor allows for a favorable physiologic hypertrophic effect from said growth hormone.

\* \* \* \* \*